United States Patent
Porat et al.

(10) Patent No.: US 7,189,512 B2
(45) Date of Patent: Mar. 13, 2007

(54) METHODS FOR VARIATION DETECTION (75) Inventors: Noga Porat, 765 San Antonio Rd., #80, Palo Alto, CA (US) 94303; Boaz Porat, Palo Alto, CA (US)

(73) Assignee: Noga Porat, Tel Aviv (IL)

( * ) Notice: Subject to any disclaimer, the term of this patent is extended or adjusted under 35 U.S.C. 154(b) by 586 days.

(21) Appl. No.: 10/370,884

(22) Filed: Feb. 20, 2003

(65) Prior Publication Data

US 2004/0166493 A1  Aug. 26, 2004

(51) Int. Cl.
*C12Q 1/68* (2006.01)
*C12P 19/34* (2006.01)

(52) U.S. Cl. ................ 435/6; 435/91.2; 435/91.51

(58) Field of Classification Search ............... 435/6, 435/91.2, 91.52
See application file for complete search history.

(56) References Cited

U.S. PATENT DOCUMENTS

| | | | |
|---|---|---|---|
| 5,270,184 A * | 12/1993 | Walker et al. ........... 435/91.2 |
| 5,556,750 A | 9/1996 | Modrich et al. | |
| 5,571,676 A | 11/1996 | Shuber ..................... 435/6 |
| 5,707,806 A | 1/1998 | Shuber ..................... 435/6 |
| 6,008,031 A | 12/1999 | Modrich et al. .......... 435/200 |
| 6,048,696 A | 4/2000 | Hoffman et al. | |
| 6,110,684 A | 8/2000 | Kemper et al. ............ 435/6 |
| 6,277,578 B1 * | 8/2001 | Shultz et al. ............. 435/6 |
| 6,322,988 B1 | 11/2001 | Dawson et al. ........... 435/6 |
| 6,548,247 B1 * | 4/2003 | Chirikjian et al. ........ 435/6 |

OTHER PUBLICATIONS

Nicholl I.D. et al., "Reconstitution of human base excision repair with purified proteins", *Biochemistry*, Jun. 17, 1997, vol. 36, No. 24. pp. 7557-7566.
Dianov G. et al., "Reconstitution of the DNA base excision-repair pathway", *Current Biology*, CB. Dec. 1, 1994, vol. 4, No. 122, pp. 1069-1076.
Dianov G. et al., "Generation of single-nucleotide repair patches following excision of uracil residues from DNA", *Molecular And Cellular Biology*, Apr. 1992, vol. 12, No. 4, pp. 1605-1612.
Zhang, Y. et al, "An amplification and ligation-based method to scan for unknown mutations in DNA", *Human Mutation* Aug. 2002, vol. 20, No. 2, pp. 139-147.
McCullough A.K. et al., Initiation of base excision repair: glycosylase mechanisms and structures, *Annual Review of Biochemistry*, 1999, vol. 68, pp. 255-285.
Bioteux S. et al., "The human OGG1 gene: Structure, functions, and its implication in the process of carcinogenesis ", *Archives of Biochemistry And Biophysics*, New York, US, vol. 377, No. 1, pp. 1-8.
PCT Search Report, Aug. 6, 2004.
Evans et al., "Going APE over ref-1", *Elsevier*, 461:83-108 (2000).

(Continued)

*Primary Examiner*—Kenneth R. Horlick
*Assistant Examiner*—Joyce Tung
(74) *Attorney, Agent, or Firm*—Mark M. Friedman (57) ABSTRACT

The present invention relates to methods for identifying variations that occur in the genome of an organism. In particular, the present invention relates to identifying variations without the need for specialized oligonucleotides complementary to each SNP and without a priori knowledge of the sequence or position of the variants.

2 Claims, 4 Drawing Sheets

OTHER PUBLICATIONS

Hall et al., "Sensitive detection of DNA polymorphisms by the serial invasive signal amplification reaction", *PNAS*, 97:8272-8277 (2000).

Schweitzer and Kingsmore, "Combining nucleic acid amplification and detection", *Current Opinion in Biology*, 12:21-27 (2001).

Kota et al., "Application of denaturing high-performance liquid chromatography for mapping of single nucleotide polymorphisms in barley (*Hordeum vulgare* L.)", *Genome*, 44:523-528 (2001).

Arnold et al., "One-Step Fluorescent Probe Product-Enhanced Reverse Transcriptase Assay", *BioTechniques*, 25:98-106 (1998).

McCullough et al., "Initiation of Base Excision Repair: Glycosylase Mechanisms And Structures", *Annu. Rev. Biochem*, 68:255-285 (1999).

Williams and David, Evidence that MutY is a monofuctional glycosylase capable of forming a covalent Schiff base intermediate with substrate DNA, Nucleic Acids Research.

Sancar, "DNA Excision Repair", *Annu. Rev. Biochem.*, 65:43-81 (1996).

Hessner et al., "Genotyping of Factor VG1691A (Leiden) without the Use of PCR by Invasive Cleavage of Oligonucleotide Probes", *Clinical Chemistry*, 46:1051-1056 (2000).

Shapero et al., "SNP Genotyping by Multiplexed Solid-Phase Amplification and Fluorescent Minisequencing", *Genome Research*, 11:1926-1934 (2001).

\* cited by examiner

METHODS FOR VARIATION DETECTION

BACKGROUND OF THE INVENTION

The DNA that makes up human chromosomes provides the instructions that direct the production of all proteins in the body. These proteins carry out the vital functions of life. Variations in DNA sequences encoding a protein may produce variations or mutations in the proteins encoded, potentially affecting the normal function of cells. Although environment often plays a significant role in disease, variations or mutations in the DNA of an individual are directly related to almost all human diseases, including infectious disease, cancer, and autoimmune disorders. Knowledge of genetics will help unravel the genetic bases of disease and be useful in treatment. For example, knowledge of human genetics has led to a limited understanding of variations between individuals when it comes to drug response—the field of pharmocogenetics. Over half a century ago, adverse drug responses were correlated with amino acid variations in two drug-metabolizing enzymes, plasma cholinesterase and glucose-6-phosphate dehydrogenase. Since then, careful genetic analyses have linked sequence polymorphisms in over 35 drug metabolism enzymes, 25 drug targets and 5 drug transporters with compromised levels of drug efficacy or safety (Evans and Relling, *Science* 296:487–91 (1999)).

Any two humans are 99.9% similar in their genetic makeup; thus, most of the sequence of the DNA of their genomes is identical. However, it is crucial to identify and understand the differences, as it is these DNA sequence differences that account for the phenotypic differences between individuals, including susceptibility to disease and response to treatment of disease. The differences in DNA appear in many forms, for example there are deletions of many-base stretches of DNA, insertions of stretches of DNA, differences in the number of repetitive DNA elements in non-coding regions, and, perhaps most importantly, changes in single nitrogenous base positions in the genome called "single nucleotide polymorphisms" (SNPs).

There are several methods for SNP genotyping known in the art. For example, DNA sequencing is well known and generally available in the art and may be used to determine the location of SNPs in a genome. See, for example, Sambrook, et al., *Molecular Cloning: A Laboratory Manual* (Cold Spring Harbor Laboratory, New York) (1989), and Ausubel, et al., *Current Protocols in Molecular Biology* (John Wiley and Sons, New York) (1997), incorporated herein by reference. Sequencing methods may be used to determine the sequence of the same genomic regions from different DNA strands where the sequences are then compared, by, for example, computer software, and the differences are noted. DNA sequencing methods may employ such enzymes as the Klenow fragment of DNA polymerase 1, Sequenase (US Biochemical Corp, Cleveland, Ohio.), Taq polymerase (Perkin Elmer), thermostable T7 polymerase (Amersham, Chicago, Ill.), or combinations of polymerases and proofreading exonucleases such as those found in the Elongase Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer, Wellesley, Mass.).

Capillary electrophoresis systems that are commercially available may be used to perform SNP analysis. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper and Sequence Naviagator, Perkin Elmer, Wellesley, Mass.) and the entire process from loading of samples to computer analysis and electronic data display may be computer controlled. Again, this method may be used to determine the sequence of the same genomic regions from different DNA strands where the sequences are then compared and the differences noted.

Alternatively, once a genomic sequence from one reference DNA strand has been determined by sequencing, it is possible to use hybridization techniques to determine differences in sequence between the reference strand and other DNA strands. These differences may be SNPs. An example of a suitable hybridization technique involves the use of DNA chips (oligonucleotide arrays), for example, those available from Affymetrix, Inc. Santa Clara, Calif. For details on the use of DNA chips for the detection of, for example, SNPs, see U.S. Pat. No. 6,300,063 issued to Lipshutz, et al., and U.S. Pat. No. 5,837,832 to Chee, et al.

Another technique suitable for the detection of SNPs in genomic DNA is the Invader technology available from Third Wave Technologies, Inc., Madison, Wis. Examples of using this technology to detect SNPs may be found, e.g., in Hessner, et al., *Clinical Chemistry* 46(8):1051–56 (2000); and Hall, et al., *PNAS* 97(15):8272–77 (2000). In the Invader process, two short DNA probes hybridize to a target nucleic acid to form a structure recognized by a nuclease enzyme. For SNP analysis, two separate reactions are run— one for each SNP variant. If one of the probes is complementary to the sequence, the nuclease will cleave it to release a short DNA fragment termed a "flap". The flap binds to a fluorescently-labeled probe and forms another structure recognized by a nuclease enzyme. When the enzyme cleaves the labeled probe, the probe emits a detectable fluorescence signal thereby indicating which SNP variant is present. One advantage of this method is that amplification of the target DNA sequence is not necessary.

Another technique for SNP analysis, rolling circle amplification, utilizes an oligonucleotide complementary to a circular DNA template to produce an amplified signal. Extension of the oligonucleotide results in the production of multiple copies of the circular template in a long concatemer. Typically, detectable labels are incorporated into the extended oligonucleotide during the extension reaction. The extension reaction can be allowed to proceed until a detectable amount of extension product is synthesized, then the extension product is analyzed by various methods, such as sequencing techniques or using microarrays.

Another technique suitable for the detection of SNPs makes use of the 5'-exonuclease activity of a DNA polymerase to generate a signal by digesting a probe molecule to release a fluorescently labeled nucleotide. This assay is frequently referred to as a Taqman assay (see, e.g., Arnold, et al., *BioTechniques* 25(1):98–106 (1998)). A target DNA containing a SNP is amplified in the presence of a probe molecule that hybridizes to the SNP site. The probe molecule contains both a fluorescent reporter-labeled nucleotide at the 5'-end and a quencher-labeled nucleotide at the 3'-end. The probe sequence is selected so that the nucleotide in the probe that aligns with the SNP site in the target DNA is as near as possible to the center of the probe to maximize the difference in melting temperature between the correct match probe and the mismatch probe. As the PCR reaction is conducted, the correct match probe hybridizes to the SNP site in the target DNA and is digested by the Taq polymerase used in the PCR assay. This digestion results in physically separating the fluorescent labeled nucleotide from the quencher with a concomitant increase in fluorescence. The mismatch probe does not remain hybridized during the elongation portion of the PCR reaction and is, therefore, not digested and the fluorescently labeled nucleotide remains quenched.

Denaturing HPLC using a polystyrene-divinylbenzene reverse phase column and an ion-pairing mobile phase also can be used to identify SNPs. In this process, a DNA segment containing a SNP is PCR amplified. After amplification, the PCR product is denatured by heating and mixed with a second denatured PCR product with a known nucleotide at the SNP position. The PCR products are annealed and are analyzed by HPLC at elevated temperature. The temperature is chosen to denature duplex molecules that are mismatched at the SNP location but not to denature those that are perfect matches. Under these conditions, heteroduplex molecules typically elute before homoduplex molecules. For an example of the use of this technique see Kota, et al., *Genome* 44(4):523–28 (2001).

SNPs can be detected using solid phase amplification and microsequencing of the amplification product. Beads to which primers have been covalently attached are used to carry out amplification reactions. The primers are designed to include a recognition site for a Type II restriction enzyme. After amplification—which results in a PCR product attached to the bead—the product is digested with the restriction enzyme. Cleavage of the product with the restriction enzyme results in the production of a single stranded portion including the SNP site and a 3'-OH that can be extended to fill in the single stranded portion. Inclusion of ddNTPs in an extension reaction allows direct sequencing of the product. For an example of the use of this technique to identify SNPs see Shapero, et al., *Genome Research* 11:1926–34 (2001).

Similarly, Shuber, U.S. Pat. No. 5,707,806, describes a method of minisequencing up to 2000 bp in the vicinity of a SNP after cleavage with mismatch repair enzymes. Methyl-directed mismatch repair enzymes, such as Mut S, Mut L, Mut H and Mut U, work as a complex to recognize and cleave at or around a mismatch (where the SNP is located if heteroduplexes have been formed). The Shuber method then employs dNTPs and ddNTPs and a polymerase to fill in the gaps. The products are then sequenced. The sequence of the sequenced products is compared to a known sequence and the differences are noted. DNA polymerases used for this method include DNA pol I, pol III, T7 DNA pol and T4 DNA polymerase.

Other techniques for SNP detection and/or genotyping are the Single Strand Conformation Polymorphisms (SSCP) technique and the Denaturing Gradient Gel Electrophoresis (DGGE) technique. In SSCP, sample and control DNAs are denatured and run on polyacrylamide gels in a non-denaturing environment. Single strands of DNA with a SNP are separated on the gel, and will show different mobility as compared to the single strands of the control DNA. The difference in mobility is caused by a conformational change of the single stranded DNA due to the single base change. However, in this method the examined DNA fragment size must be restricted to less than about 300 bp, as sensitivity of the assay is decreased if the fragment is larger.

The DGGE method is similar to SSCP in the sense that it depends on DNA denaturation by gel, but DGGE uses heat or chemical denaturants to separate the two strands of the DNA being examined. DNA fragments have different melting temperatures, determined by their nucleotide sequence. The hydrogen bonds formed between G/C melt at a higher temperature than those of T/A. When separated by electrophoresis through a gradient of increasing temperature, the control DNA and the sample DNA that contains different nucleotides will melt at different specific points on the gel, according to their melting temperatures. In addition to other drawbacks to the SSCP and DGGE processes, neither process identifies the position of the SNP—they only indicate whether one or more different nucleotides are present.

In the Single Base Primer Extension assay, double stranded sample DNA is denatured and primers complementary to the sequence are added and allowed to anneal to the DNA. The primers are usually about 20–30 nucleotides in length, and their 3' end is adjacent to the SNP. Next, DNA polymerase and ddNTPs with varying fluorescent tags are added. By identifying the 3' base added to the primer, it is possible to identify if a SNP is present. This technique, like some of those discussed previously, requires that one know a priori the location of each SNP, and requires synthesis of a specific primer for each SNP location. As an alternative to using varying tags, a mass spectrometer may be employed. Sequenom, Inc. applies this assay with the use of mass spectrometry.

Allele Specific Oligonucleotide Ligation is yet another technique employing specific primers. One primer is complementary to the target sequence 5' to and including the SNP position. The second primer is complementary to the sequence immediately 3' of the SNP position. The sample DNA is denatured and allowed to hybridize with the primers. DNA ligase is then added. If the upstream primer matches the SNP, ligation will be achieved between the two primers. If there is a mismatch—the primer does not match the SNP and ligation is not achieved. Thus, if ligation has taken place, the product will be a long single strand with the two primers connected together. Again, however, this technique requires that one know a priori the location of each SNP, and requires synthesis of two specific primers for each SNP location.

Another assay for SNPs is Allele Specific Hybridization. As with Allele Specific Oligonucleotide Ligation, sample DNA is examined by hybridization to primers. In this technique, an oligonucleotide fabricated onto a solid support covers the SNP and regions 5' and 3' of the SNP. Sample DNA is denatured and allowed to hybridize to the oligonucleotide/solid support. The sample DNA/oligonucleotide/solid support is analyzed by eluting the bound sample DNA. When the SNP position in the sample DNA is complementary to the base located at the same position on the fabricated oligonucleotide, the two strands are separated with more difficulty then when there is a mismatch. This technique can be used in conjunction with various labels. Again, however, this technique requires a priori knowledge of the SNP, sequences surrounding the SNP and the synthesis of an oligonucleotide for each SNP.

In addition to SNPs, the DNA of two organisms of the same species will differ in the number and/or position of any modified nitrogenous bases that are present. Such modifications or variations include methylations, oxidations or aminations of the basic nucleotides, including but not limited in any way to the methyladenosines and methylguanosines, 2'-O-methylcytodine, 2'-O-methyluridine, 8-oxoguanine, 8-oxoadenine, fapy-guanine, methy-fapy-guanine, fapy-adenine, aflatoxin B1-fapy-guanine, 5-hydroxy-cystosine and 5-hydroxy-uracil. The number and/or position of such modified nucleotides may be an important factor in assessing disease causing agents, particularly whether a certain chemical reagent is a carcinogen able to cause large numbers of these modified nucleotides in the DNA.

Thus, there is an interest and need in the art for a method of SNP or modified nucleotide (variation) analysis that does not require specialized primers or a priori knowledge of each SNP location. The present invention satisfies this need in the art.

SUMMARY OF THE INVENTION

The present invention relates to methods for identifying variations that occur in genomes without the need for specialized primers complementary to each SNP, or a priori knowledge of the position of each variant. The present invention comprises recognizing and binding to a mismatched base pair or modified base in a duplex DNA molecule; cleaving the mismatched or modified base; cleaving the sugar-phosphate backbone of the DNA molecule immediately 5' or 3' to the abasic residue; removing the abasic residue; generating a 3'-OH; inserting a matched base or strand terminator at the 3'-OH; ligating the DNA strand where a matched base was inserted or terminating the DNA strand where a strand terminator was inserted, and, finally, analyzing the products.

Thus, one aspect of the present invention provides methods for analyzing variants in DNA samples comprising: obtaining the DNA samples; denaturing and renaturing the DNA samples to produce a heteroduplex; recognizing mismatched base pairs in the heteroduplex; cleaving the mismatched bases to produce abasic residues; cleaving a sugar-phosphate backbone of the heteroduplex 5' or 3' to the abasic residues; removing the abasic residues; generating a 3'-OH in the sugar-phosphate backbone; inserting a dNTP or strand terminator at the site of the 3'-OH in the sugar-phosphate backbone; ligating the heteroduplex at the site of the sugar-phosphate backbone where a dNTP was inserted; terminating the heteroduplex at the site of the sugar-phosphate backbone where a strand terminator was inserted; and analyzing the heteroduplexes. In one aspect of this embodiment, the recognizing step, the cleavage steps and the removal step are performed by the same enzyme, where the enzyme is both a glycosylase and an apurinic/apyrimidinic endonuclease. In another aspect of this embodiment, the recognizing step and first cleavage step are performed by a glycosylase and the second cleavage step is performed by an apurinic/apyrimidinic endonuclease either alone (to cleave the base from the nucleotide residue and then to cleave the nucleotide residue) or with the addition of an additional enzyme such as DNA Polymerase β (when the apurinic/apyrimidinic endonuclease cleaves only the base and another enzyme is required to cleave the nucleotide residue).

Another embodiment of the present invention provides a method of analyzing modified nucleotides in a DNA sample comprising: obtaining the DNA sample; recognizing modified nucleotides in the DNA sample; cleaving the modified nucleotides to produce abasic residues; cleaving a sugar-phosphate backbone of the DNA sample 5' or 3' to the abasic residues; removing the abasic residues; generating a 3'-OH in the sugar-phosphate backbone; inserting a dNTP or strand terminator at the site of the 3'-OH in the sugar-phosphate backbone; ligating the heteroduplex at the site of the sugar-phosphate backbone where a dNTP was inserted; terminating the heteroduplex at the site of the sugar-phosphate backbone where a strand terminator was inserted; and analyzing the heteroduplexes. In one aspect of this embodiment, the recognizing step, and the cleavage steps are performed by the same enzyme, where the enzyme is both a glycosylase and an apurinic/apyrimidinic endonuclease. In another aspect of this embodiment, the recognizing step and first cleavage step are performed by a glycosylase and the second cleavage step is performed by a of apurinic/apyrimidinic endonucleases alone or with the addition of another enzyme such as DNA Polymerase β.

BRIEF DESCRIPTION OF THE FIGURES

The following figures and drawings form part of the present specification and are included to further demonstrate certain aspects of the patent invention. The invention may be better understood by reference to one or more of these drawings in combination with the detailed description of the specific embodiments presented herein.

DETAILED DESCRIPTION OF THE INVENTION

It should be apparent to one skilled in the art that various embodiments and modifications may be made to the invention without departing from the scope and spirit thereof. All publications mentioned herein are cited for the purpose of describing and disclosing reagents, methodologies and concepts that may be used in connection with the present invention. Nothing herein is to be construed as an admission that these references are prior art in relation to the inventions described herein.

The present invention relates to methods for identifying variations that occur in the genome of an organism. In particular, the present invention relates to identifying variations without the need for specialized oligonucleotides complementary to each SNP and without a priori knowledge of the sequence or position of the variants. The present invention comprises methods of recognizing and binding to a mismatched base pair or modified nucleotide in a duplex DNA molecule; cleaving the mismatched base or modified base; cleaving the sugar-phosphate backbone of the DNA molecule 5' or 3' to the abasic residue; removing the abasic residue; generating a 3'-OH in the sugar-phosphate backbone; inserting a matched base or strand terminator at the 3'-OH; ligating the DNA strand where a matched base was inserted; and terminating the DNA strand where a strand terminator was inserted. The products of the reaction are then analyzed.

As used herein, the term "SNP" or "single nucleotide polymorphism" refers to a genetic variation between individuals; e.g., a single nitrogenous base position in the DNA of organisms that is variable. As used herein, "SNPs" is the plural of SNP. Of course, when one refers to DNA herein such reference may include derivatives of DNA such as amplicons, RNA transcripts, etc.

As used herein, the term "variant" or "variation" refers to SNPs and modified nucleotides.

As used herein the term "strand terminator" refers to a molecule that, when inserted into a nucleic acid strand, terminates further polymerization of the strand.

Figure 1:
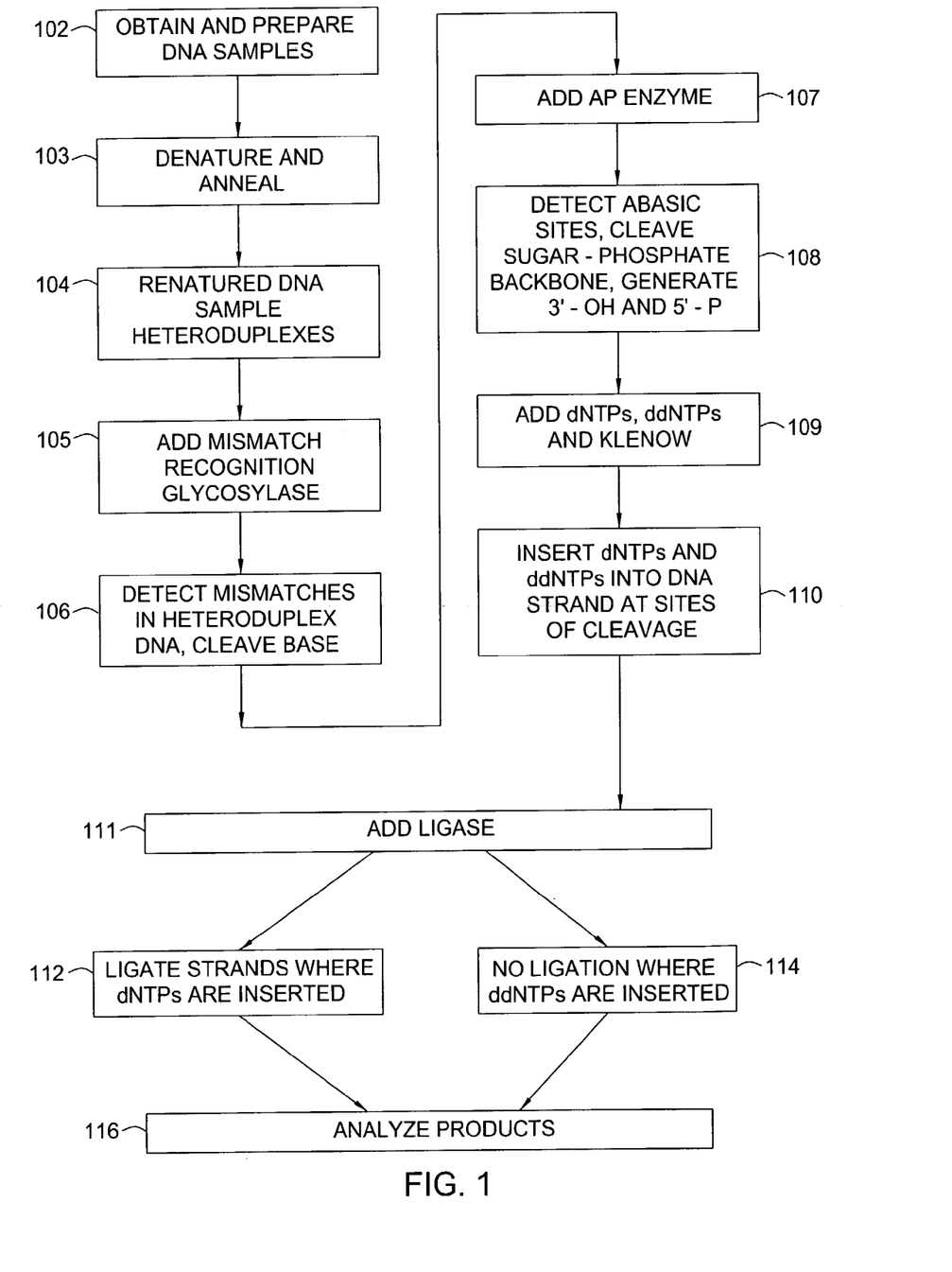
FIG. 1 is a block diagram showing the steps of one embodiment of the methods of the present invention.

FIG. 1 is a block diagram showing the steps of one embodiment of the methods of the present invention. In FIG. 1, method 100 begins by obtaining and preparing DNA samples (102). The DNA samples are then denatured and annealed in step 103, producing renatured DNA sample heteroduplexes (104). The heteroduplexes arise from the renaturing of DNA stands with mismatched bases. The bases are mismatched as the result of a strand containing one variant at a particular position annealing with a strand complementary to the other variant at that particular position. In step 105, a mismatch recognition glycosylase is added to the renatured sample such that mismatches (sites of variations or SNPs) are detected, and a base at the site of the mismatch is cleaved to produce an abasic site (106). Apurinic/apyrimidinic (AP) enzymes are added at step 107, to detect the abasic sites and to cleave the sugar-phosphate backbone at those abasic sites, leaving, preferably, 3' hydroxyl groups and 5' phosphate groups (108). Some AP enzymes may be unable to cleave the sugar-phosphate backbone after detecting the basic sites. If so, other enzymes known in the art may be used (such as DNA pol β) to cleave the sugar-phosphate backbone, remove the abasic residue and generate a 3'-OH.

Next, dNTPs, strand terminators such as ddNTPs and Klenow exo⁻ are added at step 109, inserting dNTPs or strand terminators into the DNA strands at the 3'-OH site of the cleavage (110). A ligase enzyme is added at step 111, such that DNA strands are ligated where a dNTP was incorporated (112), and DNA strands are not ligated where a strand terminator such as ddNTP was incorporated (114). Finally, the products of the (ligation) reaction are analyzed at step 116.

Figure 2:
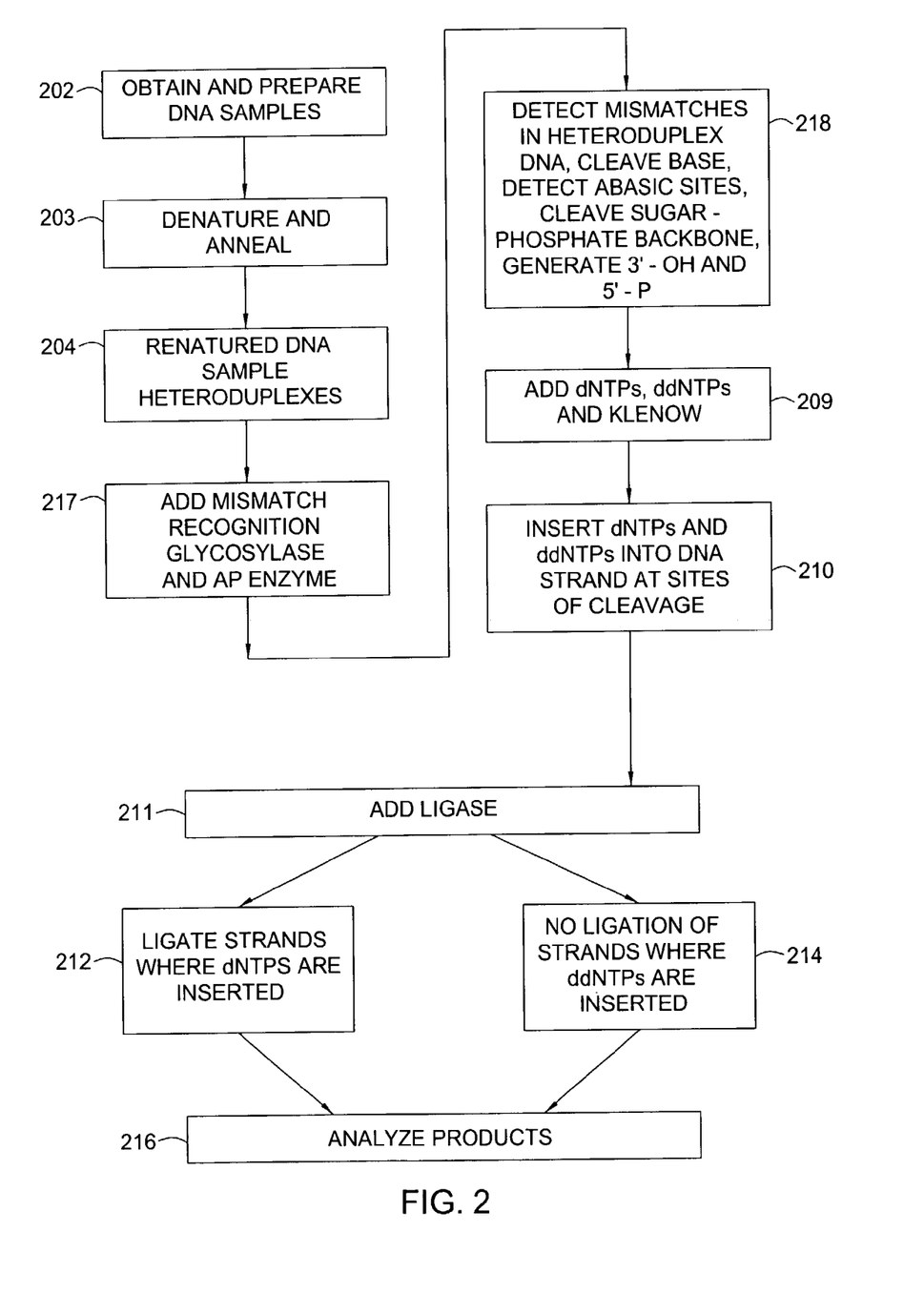
FIG. 2 is a block diagram showing the steps of another embodiment of the methods of the present invention.

FIG. 2 is a block diagram showing the steps of another embodiment of the methods of the present invention. In FIG. 2, method 200 begins by obtaining and preparing DNA samples (202). The DNA samples are then denatured and annealed in step 203, producing renatured DNA sample heteroduplexes (204). As in the embodiment in FIG. 1, the heteroduplexes arise from the renaturing of DNA stands with mismatched bases resulting from a strand containing one variant at a particular position annealing with a strand complementary to the other variant at that particular position. In step 217, a mismatch recognition glycosylase/AP enzyme is added to the renatured sample such that mismatches (sites of variations or SNPs) are detected, a base at the site of the mismatch is cleaved to produce an abasic site, the abasic sites are detected, and the sugar-phosphate backbone at those abasic sites is cleaved, leaving, preferably, 3' hydroxyl groups and 5' phosphate groups (218). Note that step 217 combines steps 105 and 107 from the method shown in FIG. 1, and that the result in 218 is a combination of the results in 106 and 108 of FIG. 1. From this point, FIGS. 1 and 2 are the same. dNTPs, strand terminators such as ddNTPs and Klenow exo⁻ are added at step 209, inserting dNTPs or ddNTPs into the DNA strands at the 3'-OH site of the cleavage (210). Ligase is added at step 211, such that DNA strands are ligated where a dNTP was incorporated (212), and DNA strands are not ligated where a strand terminator such as ddNTP was incorporated (214). Finally, the products of the (ligation) reaction are analyzed at step 216.

Figure 3:
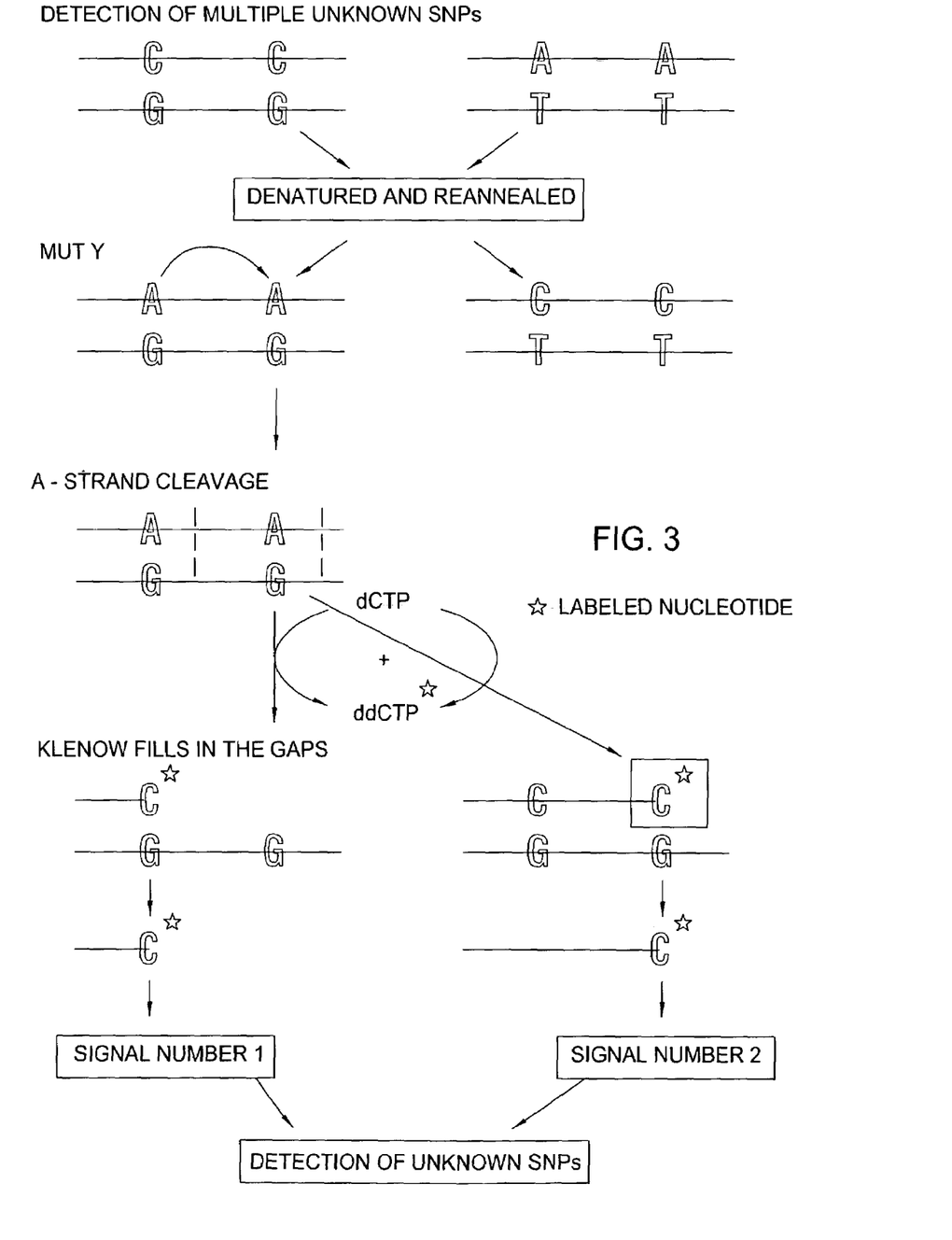
FIG. 3 is a schematic showing one embodiment of the methods of the present invention.

FIG. 3 is a schematic showing one embodiment of the methods of the present invention. In FIG. 3, two duplex DNA strands are shown. One strand contains the variation C/G at a first position, and C/G at a second position. The other strand contains the variation A/T at both these positions. The stands are denatured and annealed, forming heteroduplexes. Mut Y is added, which recognizes A/G mismatches. Mut Y cleaves the adenine base, leaving an abasic site on the "A strand", then cleaves the duplex DNA strand at the abasic site generating a one base pair gap that can be filled by Klenow exo⁻. Next, dCTP and labeled ddCTP are added, along with Klenow exo⁻ and ligase. Klenow fills in the gaps in the strands with either a dCTP, wherein the ligase can "close" or repair the strand, or a ddCTP, wherein the ligase cannot "close" the strand and the strand is terminated at the labeled ddCTP. At this point, the products are shown to be analyzed by the dideoxy method of sequencing (discussed later herein, and in Sambrook, et al., *Molecular Cloning: A Laboratory Manual* (Cold Spring Harbor Laboratory, New York) (1989)).

Figure 4:
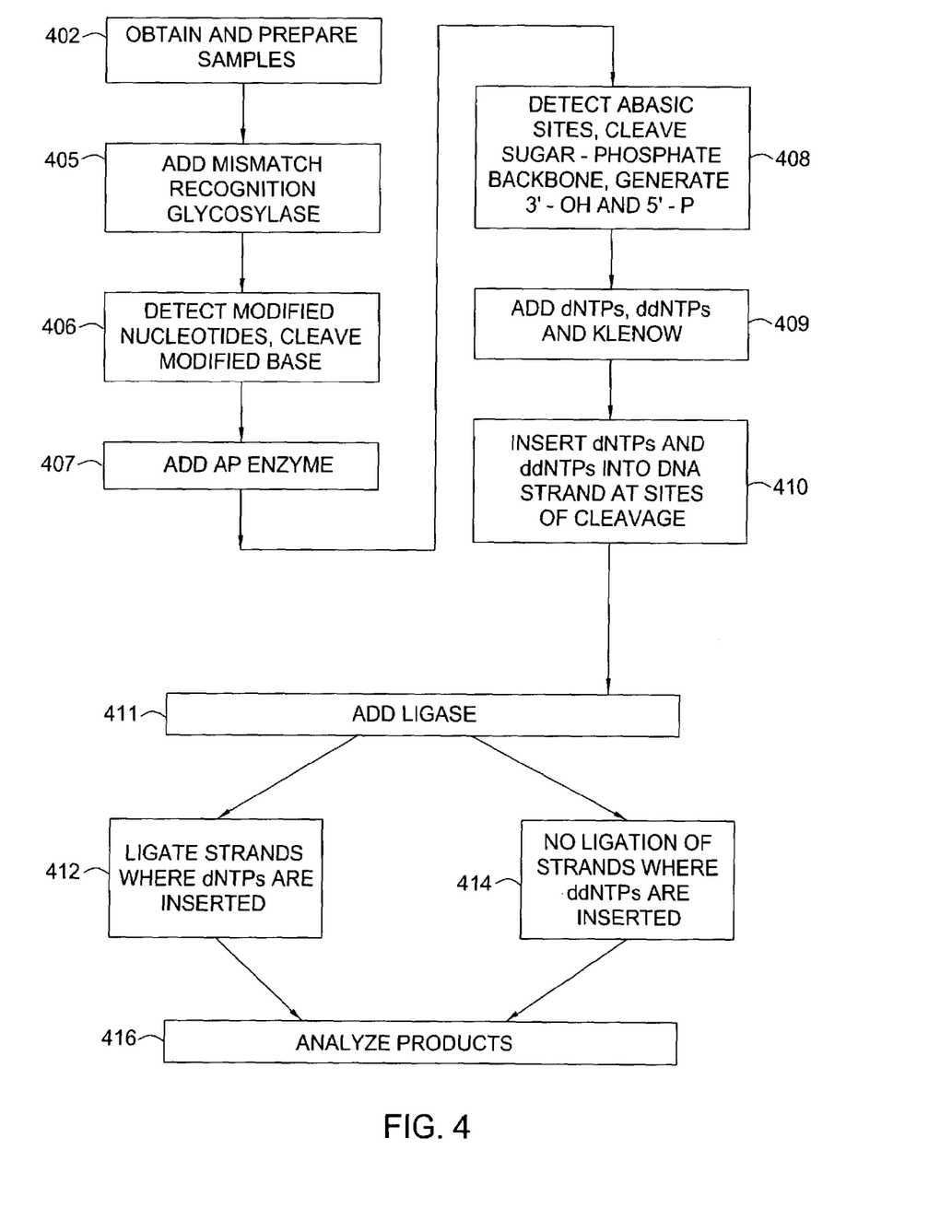
FIG. 4 is a block diagram showing the steps of yet another embodiment of the methods of the present invention.

FIG. 4 is yet another embodiment of the methods of the present invention. In this embodiment, instead of detecting SNPs, modified nucleotides, such as methylated or deaminated nucleotides, are detected. In FIG. 4, method 400 begins by obtaining and preparing DNA samples (402). In this embodiment, unlike the embodiments shown in FIGS. 1 and 2, the DNA samples are not denatured and annealed to produce a renatured heteroduplex DNA sample. In step 405, a modified nucleotide recognition glycosylase is added to the sample such that modified nucleotides are detected, and a base at the site of the modified nucleotide is cleaved to produce an abasic site (406). An apurinic/apyrimidinic (AP) enzyme is added at step 407, to detect the abasic sites and to cleave the sugar-phosphate backbone at those abasic sites, leaving, preferably, 3' hydroxyl groups and 5' phosphate groups (408).

In this embodiment, as in the embodiment of FIG. 2, an alternative would be to use a combination modified nucleotide recognition glycosylase/AP enzyme such that modified nucleotides would be detected, a base at the site of the modified nucleotide would be cleaved to produce an abasic site, the abasic sites would be detected, and the sugar-phosphate backbone at those abasic sites would be cleaved, leaving, preferably, 3' hydroxyl groups and 5' phosphate groups. That is, combining steps 405 and 407 for a combination of the results in 406 and 408. From this point, FIGS. 1, 2 and 4 are the same. dNTPs, ddNTPs and Klenow exo⁻ are added at step 409, inserting dNTPs or ddNTPs into the DNA strands at the site of the cleavage (410). Ligase is added at step 411, such that DNA strands are ligated where a dNTP was incorporated (412), and DNA strands are not ligated where a ddNTP was incorporated (414). Finally, the products of the ligation reaction are analyzed at step 416.

Preparation of Nucleic Acids for Analysis

Nucleic acid molecules may be prepared for analysis using any technique known to those skilled in the art. Preferably such techniques result in the production of a nucleic acid molecule sufficiently pure to determine the presence or absence of one or more SNPs at one or more locations in the nucleic acid molecule. Such nucleic acid extraction and preparation techniques may be found, for example, in Sambrook, et al., *Molecular Cloning: A Laboratory Manual* (Cold Spring Harbor Laboratory, New York) (1989), and Ausubel, et al., *Current Protocols in Molecular Biology* (John Wiley and Sons, New York) (1997), incorporated herein by reference.

When the nucleic acid of interest is present in a cell, it may be necessary to first prepare an extract of the cell and then perform further steps—i.e., differential precipitation, column chromatography, extraction with organic solvents and the like—in order to obtain a sufficiently pure preparation of nucleic acid. Extracts may be prepared using standard techniques in the art, for example, by chemical or mechanical lysis of the cell. Extracts then may be further treated, for example, by filtration and/or centrifugation and/or with chaotropic salts such as guanidinium isothiocyanate or urea or with organic solvents such as phenol and/or $HCCl_3$ to denature any contaminating or potentially interfering proteins. When chaotropic salts are used, it is usually desirable to remove the salts from the nucleic acid-containing sample. This can be accomplished using standard techniques in the art such as precipitation, filtration, size exclusion chromatography and the like.

In the present invention, denaturation and renaturation (annealing) of the sample DNA must be done. Denaturation is a process whereby a DNA molecule is converted from a two-stranded helical structure to a flexible, single-stranded structure, usually by applying heat. Renaturation is the reverse of the process, that is, cooling or otherwise reversing the process so that the single strands of DNA anneal to one another in a sequence specific manner to form double-stranded DNA.

In some instances, it may be desirable to extract and separate messenger RNA from cells. Techniques and material for this purpose are known to those skilled in the art and may involve the use of oligo dT attached to a solid support such as a bead or plastic surface. Suitable conditions and materials are known to those skilled in the art and may be found in the Sambrook and Ausubel references cited above. It may be desirable to reverse transcribe the mRNA into cDNA using, for example, a reverse transcriptase enzyme. Suitable enzymes are commercially available from, for example, Invitrogen of Carlsbad, Calif. cDNA prepared from mRNA may then be amplified.

It may be desirable to amplify one or more nucleic acids of interest before determining the presence or absence of one or more variations in the nucleic acid, though amplification is not a necessary step for genotyping utilizing the SNP genotyping methods of the present invention. Nucleic acid amplification increases the number of copies of the nucleic acid sequence of interest. Any amplification technique known to those of skill in the art may be used in conjunction with the present invention including, but not limited to, polymerase chain reaction (PCR) techniques. PCR may be carried out using materials and methods known to those of skill in the art.

The nucleic acids used in the methods of the invention may be labeled to facilitate detection in subsequent steps. Labeling may be carried out during an amplification reaction by incorporating one or more labeled primers into the amplified sequence. The nucleic acids may be labeled following amplification, for example, by covalent attachment of one or more detectable groups. Any detectable group known to those skilled in the art may be used, for example, fluorescent groups, ligands and/or radioactive groups. An example of a suitable labeling technique is to incorporate nucleotides containing labels into the nucleic acid of interest using a terminal deoxynucleotidyl transferase (TdT) enzyme. For example, a nucleotide—preferably a dideoxy nucleotide—containing a label is incubated with the nucleic acid to be labeled and a sufficient amount of TdT to incorporate the nucleotide. A preferred nucleotide is a dideoxynucleotide—i.e., ddATP, ddGTP, ddCTP, ddTTP, etc—having a biotin label attached.

The nucleic acid sequences to be analyzed by the methods of the present invention may be subjected to other treatments before labeling. For example, in some cases, it may be desirable to fragment the amplified sequence prior to hybridization with an oligonucleotide array. Fragmentation of the nucleic acids generally may be carried out by physical, chemical or enzymatic methods that are known in the art. Suitable techniques include, but are not limited to, subjecting the amplified nucleic acids to shear forces by forcing the nucleic acid-containing fluid sample through a narrow aperture or digesting the nucleic acid with a nuclease enzyme. One example of a suitable nuclease enzyme is Dnase I. After amplification, the nucleic acid may be incubated in the presence of a nuclease for a period of time designed to produce appropriately sized fragments. The sizes of the fragments may be varied as desired, for example, by increasing the amount of nuclease or duration of incubation to produce smaller fragments or by decreasing the amount of nuclease or period of incubation to produce larger fragments. Adjusting the digestion conditions to produce fragments of the desired size is within the capabilities of a person of ordinary skill in the art. The fragments thus produced may be labeled as described above.

Enzymes

Enzymatic reactions necessary in the methods of the present invention must accomplish several tasks. First, a DNA mismatch or variant must be detected (mismatch recognition). Second, there must be cleavage of the base and the DNA strand where the mismatch occurs (cleavage of the sugar-phosphate backbone). Third, the mismatched moieties must be excised and a properly-matched base must be inserted (excision and polymerization—i.e., repair). Finally, there must be ligation or termination of the repaired DNA strand. Various enzymes in various combinations are useful for these reactions. For information on base recognition/excision and repair, please see, for example, S. Aziz, *Annual Reviews of Biochemistry*, 65:43–81 (1996); Kelley R., et al., *Mutation Research*, 461: 83–108 (2000); Gerd, P., *Technologies for Detection of DNA Damage and Mutations*, Plenum Press, New York (1996); P. Vaughan, *Methods in Molecular Biology*, vol. 152, *DNA Repair Protocols, Prokaryotic Systems*, Humana Press (2000); L. Stephen, et al., *Annual Reviews of Biochemistry*, 68:255–285 (1999); Au et al., *Proc. Natl. Acad. Sci. USA*, 86:8877–8881 (1989); D. Sheila and W. Scott, *Nucleic Acids Research*, 26(22): 5123–5133 (1998); L. A-Lien, et al., *Proc. Natl. Acad. Sci. USA*, 89:877–8783 (1992); and U.S. Pat. No. 6,008,031.

Enzymatic systems capable for recognition and correction of base pairing errors with a DNA strand have been demonstrated in bacteria, fungi and mammalian cells. Several mismatch repair systems, other than base excision repair, have been well charactized in *E. coli*, for example the methyl-directed pathway for repair of DNA biosynthetic errors. This system processes base pairing errors within the DNA in a strand-specific manner by exploiting patterns of methylation.

One example of a mismatch repair enzyme is Mut Y. Mut Y is a glycosylase enzyme with a possible associated apurinic/apyrimidinic (AP) endonuclease (lyase) activity. Mut Y recognizes A/G mismatches in duplex DNA. DNA glycosylases cleave the glycosylic bond between the sugar and the base moieties of the DNA strand. Glycosylases are small enzymes (Mr=around 20,000 to 30,000) of narrow substrate specificity and have no cofactor requirement. DNA glycosylases cleave the glycosylic bond at the nitrogenous base, generating an apurinic/apyrimidinic (AP) (abasic) site.

Once the base is cleaved by the glycosylase, AP endonucleases then cleave the phosphate backbone 3' or 5' to the abasic site. Two classes of AP enzymes have been well described. Class I AP endonucleases hydrolyze the phosphodiester bond 3' to the abasic sugar by β-elimination. This leaves a 3'-blocking group moieties and 5'-P termini. Class II AP endonucleases cleave the phosphodiester bond 5' to the abasic sugar, leaving 3'-OH and 5'-blocking groups moieties. In addition, class I enzymes may have both glycosylase and AP endonuclease activities. Class I and II AP enzymes are preferred for use in the present invention as, apart or combined, they generate 3'-OH and 5'-P termini, suitable for polymerization.

Enzymes having both glycosylase and AP endonuclease activities which generate 3'-OH and 5'-P (with or without the requirement for piperidine, in reactions that are known in the art) are even more preferred and can be used directly in the methods of the present invention. Enzymes having both glycosylase and AP endonuclease activities that generate 3'-blocking groups including 3'-phosphate, 3'-phosphoglycolate and 4-hydroxy-2-pentenal can be used as long as the reaction is then followed by cleavage with APE (Ape1/Ref-1), a class II AP endonuclease which also possesses DNA 3'-repair diesterase or phosphatase activities and generates 3'-OH termini, suitable for DNA polymerization. Other AP endonucleases that can be used as an alternative to APE (Ape1/Ref-1), include but are not limited to; Exo A, Rrp 1, Arp, Apn2, BAP1, rAPE and chAPE1. These enzymes are known to have a robust 3' repair diesterase activity.

Enzymes with glycosylase activity only must be combined with a separate AP endonuclease to accomplish mismatch recognition, base cleavage and DNA strand cleavage. For example, glycosylase enzymes with no associated AP endonuclease activity may also be used with APE (Ape1/Ref-1). APE's 5' AP endonuclease activity (requiring $Mg^{2+}$) cleaves 5' to the AP site generating a 3'-OH and a 5'deoxyribose phosphate moiety (dRP), which can then be excised by DNA polymerase β (pol β). Pol β inserts the correct base and ligase restores the strand break.

Additionally, other AP endonucleases include Endonuclease IV, a class II AP endonuclease, and Endonucleases III and VIII, class I AP endonucleases. It is an important aspect of the present invention that the AP endonucleases (as well as the other enzyme components) not have any 3' or 5' exonuclease activity. Further, AP endonucleases that do not generate a 3'-OH and a 5'-P must be used in conjunction with another enzyme of enzymes to ultimately generate a 3'-OH and a 5'-P. One skilled in the art knows what enzymes to combine to achieve specific goals for detecting various modified nucleotides or mismatches, excising the modified nucleotides or mismatches, and generating a 3'-OH and a 5'-P, suitable for further polymerization.

There are several different substrate-specific DNA glycosylases, for example, uracil-DNA glycosylase; hypoxanthine DNA glycosylase; 3-methyladenine DNA glycosylases I and II; urea DNA glycosylase; PD DNA glycosylase; and TDG. Uracil-DNA glycosylase cleaves the uracils misincorporated into DNA by DNA polymerases, or that occur due to deamination of cytosine. Hypoxanthine DNA glycosylase recognizes DNA at hypoxanthine residues caused by spontaneous deamination of adenine.

Among the DNA glycosylases with known associated AP activity that hydrolyze the phosphodiester bond 3' to the abasic sugar are those which help protect cells from oxidative stress, such as hOGG1 and FPG. hOGG1 is an 8-oxoguanine-DNA glycosylase. hOGG1 releases 8-oxoguanine from double stranded DNA, generating an AP site, which is then cleaved 3' to the AP site leaving 5'-P and a 3' opened-ring. hOGG1 also recognizes and removes formamido-pyrimidine (FaPy)-guanine and methy-fapy-gaunine. FPG (formamido-pyrimidine (FaPy) DNA glycosylase) acts similarly to hOGG1 but cleaves both 3' and 5' to the AP site, leaving phosphoryl groups; FPG removes the faulty base entirely, leaving a one base gap. FPG also recognizes 8-oxoguanine, 8-oxoadenine, fapy-guanine, methy-fapy-guanine, fapy-adenine, aflatoxin B1-fapy-guanine, 5-hydroxy-cystosine and 5-hydroxy-uracil.

Thymine-DNA glycosylase enzyme (TDG) recognizes T/G mismatches and cleaves the strand containing the T, correcting to C/G. At G/G mismatches TDG cleaves either strands, but not simultaneously, leaving a nicked DNA.

Another enzyme useful in the present invention is DNA polymerase. DNA polymerases catalyze the synthesis of DNA from deoxyribonucleoside triphosphates in the presence of a nucleic acid primer. DNA polymerases are generally grouped into two categories. Family A includes *E. coli* and various other bacterial polymerases I, *Thermus aquaticus* Taq polymerase, some bacteriophage DNA polymerases, and yeast mitochondrial polymerase gamma. Family B includes the polymerases of higher eukaryotes, yeast polymerases I to III, archaebacterial polymerases, and many viral polymerases. Klenow enzyme is the name often used for the larger (75 kD) of the two fragments formed by the treatment of *E. coli* DNA polymerase I with subtilisin in the presence of DNA. The Klenow enzyme retains the 5' to 3' polymerase activity and the single-stranded specific 3' to 5' exonuclease activity, but lacks the 5' to 3' exonuclease activity of DNA polymerase I. Klenow fragment exo⁻ lacks the 3' to 5' exonuclease activity besides already lacking the 5' to 3' exonuclease activity and is therefore particularly useful in the methods of the present invention. Any polymerases which lack both exonuclease activities may be used in the present invention. The DNA polymerase used in the present invention adds dNTPs and ddNTPs or other DNA polymerization and strand terminators (labeled or not) to the DNA strands, allowing the strands to be analyzed, by various techniques. See, generally, Schweitzer B. and Kingsmore S., *Current opinions in biotechnology*, 12:21–27 (2001).

Ligases are enzymes that catalyze the ligation of molecules with the concomitant breaking of the diphosphate linkage in a nucleoside triphosphate. Ligases useful in the present invention include T4 DNA Ligase, DNA ligase I, III or III/XRCC.

Analysis Techniques

The products resulting from the base recognition, base cleavage, strand cleavage and ligation or termination reactions can be analyzed in a number of ways known in the art. In such methods, the DNA strands being analyzed terminate at sequence-specific positions, but the terminations occur randomly along the length of the DNA, that is, the population of DNA strands to be analyzed is a set of nested fragments whose lengths are determined by the distribution of strand terminators along the length of the original DNA strand.

One method of analysis useful in the present invention is a modified Sanger dideoxy-mediated chain-termination method, where the population of DNA fragments is resolved by electrophoresis and compared to a known sequence of the strand. As discussed previously, in the methods of the present invention, DNA strands that have nicks in them from the removal of abasic or modified nucleotides are reacted with 2'-dNTP, a small proportion of 2',3'-ddNTP (preferably labeled), DNA polymerase and ligase. There is a competition between the dNTP and the ddNTP for incorporation into the strand. If a dNTP is incorporated into the DNA strand by the polymerase, the ligase will ligate or "close" the strand. If instead a ddNTP is incorporated in the strand by the polymerase, the DNA strand will be terminated—the ligase is unable to ligate or "close" the strand. The products of the reaction are a population of DNA strands whose lengths are determined by the 5' terminus of the strand (which should be the same in all cases) and the sites of strand termination (ddNTP incorporation). In a reaction where dCTP and ddCTP have been used, for example, the termination points should correspond to all places where an A/G mismatch occurred (if the mismatch recognition enzyme recognizes and cleaves the A base and the A strand), or at all places where a modified C occurred (if the modified nucleotide recognition enzyme recognizes and cleaves the modified C and the C strand). The products can be separated by electrophoresis, and the location of each band can be ascertained by the label used on the ddNTP. If the products are loaded into a gel adjacent to those of a sequencing gel for that strand or compared to a known sequence for the strand, the locations of the SNPs or variations can be determined.

Another method of analysis useful in the present invention is analysis by microarray. Microarrays typically are substrates having a plurality of detection probes immobilized thereon. Each detection probe is at a known location. The detection probes can be at any density that is useful to practice the invention. The detection probes correspond to the nucleic acid sequence being analyzed for SNPs or variations; thus, microarray analysis can be done only when the sequence of the DNA being analyzed is known. Preferably, at least one set of detection probes is complementary to the sequence being analyzed and at least one set, preferably three sets, of detection probes are non-complementary to the sequence being analyzed. Preferably, the probes that are non-complementary are designed to be a one-base mismatch to the reference sequence. Methods for designing, selecting and making probe sets are described in, for example, U.S. Pat. Nos. 5,143,854; 5,424,186; 5,445,934; 5,744,305; 6,040,138; 6,040,193.

For example, one strategy for array design provides an array that is subdivided into sets of four probes (oligonucleotides of differing sequence), although in some situations, more or less probes per set may be appropriate. In a typical embodiment, one probe in each probe set comprises a plurality of bases exhibiting perfect complementarity with the selected reference sequence. In this probe of the set, complementarity with the reference sequence exists throughout the length of the probe. For the other three probes in the set, complementarity with the reference sequence exists throughout the length of the probe except for an interrogation position, which typically consists of one nucleotide base at or near the center of probe. For example, for an A nucleotide in the reference sequence, the corresponding probe with perfect complementarity from the probe set has its interrogation position occupied by a T, the correct complementary base. The other probes from the set have their respective interrogation positions occupied by A, C, or G—a different nucleotide in each probe. Thus, there are four probes corresponding to each nucleotide of interest in the reference sequence.

Hybridization assays on substrate-bound oligonucleotide arrays involve a hybridization step and a detection step. In the hybridization step, a hybridization mixture containing the DNA product being analyzed and, typically, an isostabilizing agent, denaturing agent or renaturation accelerant, is brought into contact with the probes of the array and incubated at a temperature and for a time appropriate to allow hybridization between the DNA product and any complementary probes. Usually, unbound DNA product molecules are then removed from the array by washing with a wash mixture, leaving only DNA molecules that have bound to the array. The arrays are read by comparing the intensities of labeled DNA product nucleotides that are bound to the probes on the array after hybridization. Specifically, a comparison is performed between each probe (e.g., probes differing in their interrogation position by an A, C, G and T) of each probe set. For a particular probe set, the probe position showing the greatest hybridization signal is called as the nucleotide present at the position in the target sequence corresponding to the interrogation position in the probes. Clearly, of the four probes in a set, most of the time only one will exhibit a perfect match with the DNA product and the other three probes will be mismatches. However, at the site of the SNP, two probes will exhibit perfect matches to the DNA product (corresponding to each SNP allele) whereas the other two probes of the set exhibit at least a one base pair mismatch. The probes exhibiting the best match usually produces substantially greater hybridization signal than the other probes in the column and are thereby easily identified.

Alternatively, in methods used to analyze SNPs and/or modified nucleotides, one may be interested less in the position of the SNPs or modified nucleotides and more in the number or quantity of such nucleotides. Thus, in such methods, use of dNTPs and labeled ddNTPs with subsequent sequence analysis by gel or capillary electrophoresis, microarray techniques or other techniques known in the art are not necessary. Instead, labeled dNTPs can be added without ddNTPs and chain termination, effectively adding a labeled nucleotide at every position where a modified nucleotide was detected and repaired. The quantity of the label incorporated is a measure of the number of positions of modified nucleotides present in the sample.

Applications

Applications for the methods of the present invention include finding new disease-causing genes by detecting SNPs, determining SNP maps in a fashion similar to creating restriction maps, and genotyping individuals—which is an essential for pharmacogenomics and molecular diagnostics. SNP maps can be used to examine individuals, to scan populations of individuals, or to compare differences between species. In fact, SNP maps can be used in the same ways that restriction maps have been used in the past. For example, a SNP map determined for an individual at one point in time could be update regularly to detect changes, particularly if such changes have been shown to be linked to and are able to predict a pre-cancerous or cancerous condition. Moreover, the locations of such SNPs could be the targets for future gene therapy.

Another application of the present invention is the detection of modified bases in DNA, which have not undergone repair. This may allow a better evaluation of DNA repair rates in different individuals or species; thus detecting abnormalities in repair mechanisms. Furthermore, the methods of the present invention could be used in assaying various carcinogenic reagents to asses such reagnets' strength as carcinogens. Such evaluations may also be applied to determine UV irradiation loads in various individuals by examining the rate of damage the UV radiation causes to the DNA of the cells.

Other applications of the methods of the present invention should occur to those skilled in the art.

EXAMPLES

Two 100 bp synthetic oligonucleotides were hybridized to create three A/G mismatches at bases 36, 57 and 87. The purpose was to show that a dCTP (C) can replace the dATP (A) at the mismatch site after the adenine base undergoes cleavage with Mut Y. In addition, T4 Polynucleotide Kinase, Klenow fragment exo$^-$, and T4 DNA Ligase were added to repair the cleaved mismatches.

DNA sample reactions contained 100 ng of the double stranded oligonucleotide substrate, 1× Klenow buffer (33 mM Tris-acetate (pH 7.9), 10 mM Mg-acetate, 66 mM K-acetate and 0.1 mg/ml BSA), 2 units of Mut Y and water to a final volume of 15 µl. The samples were incubated at 37° C. for up to 7 hours. The samples were then heated at 65° C. for 10 minutes. Next, 15 units of polynucleotide kinase was added and the samples were incubated at 37° C. for 1 hour. Next, 7.5 units of Klenow exo$^-$; dCTP, ddCTPmM, and dATP each at a final concentration 0.8–12.0 mM; buffer (33 mM Tris-acetate (pH 7.9), 10 mM Mg-acetate, 66 mM K-acetate and 0.1 mg/ml BSA), and water were added to the samples to achieve a final volume of 25 µl. The samples were incubated at 37° C. for 1 hour and then heated at 65° C. for 10 minutes. The heating step was followed by the addition of 7.5 units of T4 DNA ligase, and incubation at 22° C. for 40 minutes. The sample reactions were terminated by addition of 5 µl 0.6 M NaOH, 11 µl 97% formamide, and 2 µl 0.02% bromophenol blue, followed by heating at 95° C. for 10 minutes. The products were resolved by electrophoresis on a 12% denaturing polyacrylamide gel (8 M urea). After running, the gel was stained with 0.5 µg/ml ethidium bromide for 10 minutes.

Control samples were reacted with Mut Y as above, but were treated differently after the cleavage reaction. To one control, only 0.8–12 mM dCTP was added, with no enzymes. This sample was frozen until the sample reactions were terminated. In a second control, 0.8–12 mM dCTP was added (again, no enzymes), and this control sample was incubated at 37° C. with the other samples until the reactions were terminated. A third control followed the same reaction protocol as the test samples, adding the three enzymes (kinase, Klenow exo⁻ and ligase), but omitting the dCTP. Finally three other controls followed the same reaction protocol, but were supplemented with 0.8–12 mM of one of each of dATP, dGTP, or dTTP, instead of dCTP.

Results showed that a complete reaction, as were performed in the test samples, produced a thick 100 bp band (reconstructed) compared to the control samples to which dCTPs alone were added. It did not matter whether the control samples had been frozen or further incubated at 37° C. The control in which enzymes alone had been added (but without dCTP), did not show reconstruction of the 100 bp band. Finally, controls supplemented with the deoxynucleotide triphosphates other than dCTP did not show reconstruction of the 100 bp band.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, composition of matter, process or assay to the objective, spirit and scope of the present invention. All such modifications are intended to be within the scope of the invention.

All references cited herein are to aid in the understanding of the invention, and are incorporated in their entireties for all purposes.

We claim:

1. A method of analyzing and identifying variants in DNA samples by utilizing the specificity of the base excision repair (BER) system enzymes comprising:
   (a) obtaining the DNA samples;
   (b) denaturing and renaturing the DNA samples to produce a heteroduplex;
   (c) recognizing mismatched base pairs in the heteroduplex;
   (d) cleaving the mismatched bases to produce abasic residues;
   (e) cleaving a sugar-phosphate backbone of the heteroduplex 5' and/or 3' to the abasic residues, wherein the recognizing step (c) and the cleavage steps (d) and (e) are performed by Mut Y;
   (f) removing the abasic residues;
   (g) generating a 3'-OH and a 5'-P site in the sugar-phosphate backbone leaving a single nucleotide gap in the DNA;
   (h) adding Klenow exo, dNTP and labeled ddNTP to insert a dNTP or a labeled ddNTP at the single nucleotide gap at the 3'-OH site of the sugar-phosphate backbone;
   (i) adding DNA ligase to ligate the heteroduplex where a dNTP was inserted;
   (j) terminating the heteroduplex where ddNTP was inserted; and
   (k) identifying the variants by performing urea electrophoresis (PAGE) to determine the length of the heteroduplexes and to identify the labeled ddNTP inserted;
   (l) interpreting the results utilizing the specificity of the base excision repair (BER) system enzymes to deduce original variants,
   wherein when Mut Y is used and ddCTP is detected as the result of the electrophoresis (PAGE), then A/G is deduced to be the original variants; if ddGTP is detected as the result of the electrophoresis (PAGE), then A/C is deduced to be the original variants.

2. A method of analyzing and identifying variants in DNA samples by utilizing the specificity of the base excision repair (BER) system enzymes comprising:
   (a) obtaining the DNA samples;
   (b) denaturing and renaturing the DNA samples to produce a heteroduplex;
   (c) recognizing mismatched base pairs in the heteroduplex;
   (d) cleaving the mismatched bases to produce abasic residues;
   (e) cleaving a sugar-phosphate backbone of the heteroduplex 5' and/or 3' to the abasic residues, wherein the recognizing step (c) and cleavage step (d) are performed by Thymine-DNA glycosylase (TDG) and cleavage step (e) is performed by APE;
   (f) removing the abasic residues;
   (g) generating a 3'-OH and a 5'-P site in the sugar-phosphate backbone leaving a single nucleotide gap in the DNA;
   (h) adding Klenow exo⁻, dNTP and labeled ddNTP to insert a dNTP or a labeled ddNTP at the single nucleotide gap at the 3'-OH site of the sugar-phosphate backbone;
   (i) adding DNA ligase to ligate the heteroduplex where a dNTP was inserted;
   (j) terminating the heteroduplex where ddNTP was inserted; and
   (k) identifying the variants by performing urea electrophoresis PAGE) to determine the length of the heteroduplexes and to identify the labeled ddNTP inserted;
   (l) interpreting the results utilizing the specificity of the base excision repair (BER) system enzymes to deduce original variants;
   wherein when TDG is used and a ddCTP is detected as the result of the electrophoresis (PAGE), then T/G is deduced to be the original mutation; if a ddATP is detected as the result of the electrophoresis (PAGE), then T,T is deduced to be the original variants if a ddGTP is detected as the result of the electrophoresis (PAGE), then T/C is deduced to be the original variants.

* * * * *